Figure 1:
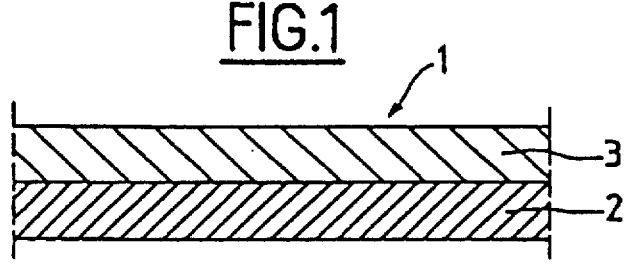

United States Patent [19]
Koczab

[11] Patent Number: 5,669,798
[45] Date of Patent: Sep. 23, 1997

[54] COMPOSITE NONWOVEN MATERIAL PROCESS OF MANUFACTURE AND ITS APPLICATION TO ANY ABSORBENT ARTICLE OF HYGIENE

[75] Inventor: Jean-Pierre Koczab, Bondues, France

[73] Assignee: Peaudouce, Linselles, France

[21] Appl. No.: 564,177

[22] PCT Filed: Jun. 14, 1995

[86] PCT No.: PCT/FR94/00710

§ 371 Date: Jan. 18, 1996

§ 102(e) Date: Jan. 18, 1996

[87] PCT Pub. No.: WO94/29506

PCT Pub. Date: Dec. 22, 1994

[30] Foreign Application Priority Data

Jun. 16, 1993 [FR] France ................... 93 07239

[51] Int. Cl.$^6$ .................. A61F 13/54; B32B 5/08; B32B 7/10; B32B 7/12; B32B 31/20
[52] U.S. Cl. .................. 442/362; 156/291; 156/308.2; 442/364; 442/389; 442/393; 442/411; 428/340; 604/366; 604/384; 604/385.1
[58] Field of Search .................. 156/291, 308.2; 442/362, 364, 389, 393, 411; 428/340; 604/366, 384, 385.1

[56] References Cited

U.S. PATENT DOCUMENTS

| | | |
|---|---|---|
| 4,826,498 | 5/1989 | Koczab . |
| 5,143,779 | 9/1992 | Newkirk et al. . |

FOREIGN PATENT DOCUMENTS

| | | |
|---|---|---|
| 0232729 | 8/1990 | European Pat. Off. . |
| 0 516 877 | 12/1992 | European Pat. Off. . |
| 0 532 005 | 3/1993 | European Pat. Off. . |
| 2588285 | 10/1987 | France . |
| 2 085 358 | 4/1982 | United Kingdom . |
| WO87/07177 | 12/1987 | WIPO . |
| WO88/05269 | 7/1988 | WIPO . |
| WO91/14414 | 10/1991 | WIPO . |

*Primary Examiner*—James C. Cannon
*Attorney, Agent, or Firm*—Burns, Doane, Swecker & Mathis LLP

[57] ABSTRACT

A composite nonwoven material comprises at least one layer (2) of a carded voile of hydrophobic thermoplastic fibers, the said fibers being partially disoriented in at least a proportion of the thickness of the voile so that a proportion of the said fibers has an angular orientation in relation to the main plane of the fibers of the said voile, and a layer (3) made of voile of nonwoven of noncarded type of hydrophobic thermoplastic fibers, the fibers of at least one of the layers being chosen from fibers with a low melting point, two-component fibers, mixtures of such fibers with fibers of high melting point and fibers mixed with a binder or one face of the voile of one of the layers is coated with a binder, the layers being joined together by heat-melting.

19 Claims, 2 Drawing Sheets

COMPOSITE NONWOVEN MATERIAL PROCESS OF MANUFACTURE AND ITS APPLICATION TO ANY ABSORBENT ARTICLE OF HYGIENE

The invention relates generally to a new nonwoven material which, when employed as surface voile or sheet or as a supplement to the surface sheet as strip in the crotch region in an absorbent article of hygiene such as a diaper or dressing for the incontinent, allows better isolation of the user's skin from the absorbent part of the article of hygiene. In particular, this new material is favorable to the time taken by the body fluids to pass through and to resistance to rewetting, and does not become fluffy.

In general, absorbent articles of hygiene such as diapers and dressings for the incontinent, comprise an outer layer of liquid-impervious material, a pad made of absorbent material and a surface of voile or sheet which is permeable to body fluids such as urine, of size and shape which are similar to those of the impervious outer layer of the article. The purpose of this surface voile which is permeable to body fluids is to isolate the skin from the moist and absorbent pad. Consequently, the surface sheet must have an appropriate degree of softness and provide the required isolation between the skin and the absorbent pad. The purpose of the absorbent pad is to absorb the fluids and consequently it must have a high rate of absorption and a high absorbency. A particularly effective absorbent pad is described in document EP-A-0,232,729. This absorbent pad or mat is made up of a sheet of long absorbent fibers, the faces of said sheet being lined with a layer of cellulose wadding. The sheet lined with the layers of wadding is needled from both sides.

In the absorbent articles of hygiene such absorbent mats or pads are covered by a surface sheet or by a strip in the crotch region, generally made of an unwoven material, the purpose of which is to isolate the skin from the absorbent pad and which must provide a pleasant contact with the skin and the required isolation from the absorbent pad. These surface voiles or sheets and strips in the crotch region must exhibit, as essential properties, a pleasant contact with the skin, a high rate of permeation by the body fluids, a good resistance to rewetting and must not become fluffy.

Document FR-A-2,588,285 describes a multilayer nonwoven textile which has at least two layers of nonwoven voile, one of the layers being made of fibers of bilobar cross-section and the other layer being made of fibers of trilobar cross-section. Each voile layer is preferably obtained by the technique of bonding when spinning (spun-bonded) and the two voile layers are joined together to form the multilayer nonwoven by heat-bonding in the compacted and noncontinuous regions.

Document WO 87/07117 describes an absorbent article of hygiene comprising an absorbent body surrounded by a cover. This surface cover or voile consists of two layers of nonwoven material. The first layer of nonwoven material, in contact with the user's skin, consists of a thin layer of spun-bonded fibrous fabric made of a hydrophobic material, and the second layer in contact with the absorbent body is a hydrophobic fibrous layer of melt-bonded fibre fabric, similar in construction to the first layer. These two surface voile layers are not bonded together in the region intended to come into contact with the user's body.

Document WO 88/05269 relates to a surface voile for a disposable absorbent article consisting of at least two layers of nonwoven material which may be identical or different and which are joined together by lines of adhesive forming an open pattern.

A new composite nonwoven material has also recently been developed, comprising at least one first layer consisting of a nonwoven (preferably spun-bonded) and, on this first layer, a sheet of fibers of carded type, the sheet of fibers of carded type being bonded to the base layer by needling.

Another recently developed composite nonwoven material comprises a first layer made of a nonwoven (preferably spun-bonded), a sheet of fibers of carded type and a second layer made of a nonwoven (preferably spun-bonded) of smaller weight per unit area than the first layer of nonwoven, the sheet of fibers of carded type being arranged between the first and the second layer of nonwoven, and the whole being bonded by needling.

These materials exhibit excellent body fluid pass-through times and an excellent resistance to rewetting. However, these materials have a pronounced tendency to become fluffy when employed as surface voile or crotch strip in absorbent articles of hygiene such as diapers.

Document WO 91/14414 describes a composite nonwoven comprising a first layer consisting of at least 75% by weight of hydrophobic thermoplastic fibers and a second layer consisting of a mixture of approximately 20 to 70% by weight of hydrophobic thermoplastic fibers and approximately 30 to 80% by weight of hydrophilic natural fibers, the layers being secured to each other by molten parts. The layers may be made from carded or uncarded voiles and the hydrophobic thermoplastic fibers may be chosen from polyolefin, polyester or twin-component fibers.

The objective of the present invention is therefore to provide a composite nonwoven material which, when employed as a surface sheet or crotch strip in an absorbent article of hygiene, has an excellent rate of crossing by body fluids, a good resistance to rewetting and which does not become fluffy.

Another objective of the invention is to provide a process for the manufacture of such a composite nonwoven material.

Finally, an objective of the present invention is to provide an absorbent article of hygiene comprising a surface sheet or a crotch region strip made of such a composite nonwoven material.

According to the present invention a composite nonwoven material which is permeable to body fluids is produced, characterized in that it comprises at least one first layer of a carded voile of hydrophobic thermoplastic fibers, these fibers being partially disoriented in at least a proportion of the thickness of the voile so that a proportion of these fibers has an angular orientation in relation to the main plane of the fibers of the carded voile and a second layer made of a voile of nonwoven of noncarded type, of hydrophobic, thermoplastic fibers, the fibers of at least one of the layers being chosen from fibers with a low melting point, two-component fibers, mixtures of such fibers with fibers of high melting point, fibers mixed with a binder such as a heat-reactivable adhesive or a powder with a low melting point, and mixtures of such fibers with fibers of high melting point, or at least one of the layers is made of a voile one face of which is coated with a binder, the layers being bonded to each other solely by heat-melting.

The invention also provides a process for the manufacture of a composite nonwoven material comprising the stages consisting in:

forming a carded voile of hydrophobic thermoplastic fibers;

partially disorienting the fibers of the carded voile to obtain in at least a proportion of the thickness of the carded voile an angular orientation of a proportion of the fibers in relation to the main plane of the fibers of the carded voile;

forming a voile of nonwoven of noncarded type, of hydrophobic thermoplastic fibers;

superposing the carded voile with partially disoriented fibers and the voile made of nonwoven of noncarded type to obtain a first layer of voile with partially disoriented fibers on a second layer of the voile made of nonwoven of noncarded type, the fibers of at least one of the said layers being chosen from fibers with a low melting point, two-component fibers, mixtures of such fibers with fibers of high melting point, and fibers mixed with a binder such as a heat-reactivable adhesive or a powder of low melting point; and binding the layers to each other by heat-melting, for example by reactivation by means of hot air passing through the layers.

Another embodiment of the process according to the invention comprises the stages consisting in:

forming a carded voile of hydrophobic thermoplastic fibers;

partially disorienting the fibers of the carded voile to obtain in at least a proportion of the thickness of the carded voile an angular orientation of a proportion of the fibers in relation to the main plane of the fibers of the carded voile;

forming a voile made of nonwoven of noncarded type, of hydrophobic thermoplastic fibers;

coating one of the faces of one of the said voiles with a binder, for example a heat-reactivable adhesive;

superposing the carded voile with partially disoriented fibers and the voile made of nonwoven of noncarded type to obtain a first layer of carded voile and a second layer of nonwoven of noncarded type so that the said binder-coated face forms an interface between the said layers; and bonding the layers to each other by heat-melting.

According to the present invention an absorbent article of hygiene is also produced, such as a diaper which comprises an outer layer of material which is impervious to body fluids, an absorbent pad which is permeable to body fluids and on this absorbent pad either a surface sheet or a surface sheet and a crotch region strip, the surface sheet, when employed by itself, consisting of the composite nonwoven material according to the invention and the crotch region sheet consisting of the composite nonwoven material according to the invention and the surface sheet, of a nonwoven, preferably hydrophobic, when a crotch region strip and a surface sheet are employed together. In the article of hygiene the surface sheet or the crotch region strip consisting of the composite material according to the invention is arranged so that the layer of carded voile is in direct contact with the inner surface of the absorbent pad and consequently the layer made of nonwoven of noncarded type is in direct contact with the user's skin or in contact with the outer surface of the surface sheet in the case where the article comprises a surface sheet made of nonwoven.

In a recommended embodiment the invention provides an absorbent article of hygiene such as a diaper, which comprises an outer layer made of material which is impervious to body fluids, an absorbent pad which is permeable to body fluids, attached to the outer layer, the outer layer and the absorbent pad comprising widened opposing end parts joined by a narrower crotch region, a surface sheet, preferably hydrophobic, a crotch region strip, permeable to body fluids, arranged between the pad and the surface sheet and similar in width to the crotch region of the pad and with a length at least equal to that of the pad, this crotch region strip consisting of the composite nonwoven material according to the invention, the layer made of carded voile being directly in contact with the inner surface of the absorbent pad.

In a particularly recommended embodiment the surface sheet comprises a medium lengthwise cutout forming an opening, preferably of oblong shape.

In another embodiment an intermediate strip, made of nonwoven, similar in size to that of the crotch region strip, is arranged directly on the crotch region strip, below the surface sheet.

The crotch region strip is generally bonded to the absorbent pad by any appropriate means, and in particular by adhesive bonding to the edge of the absorbent pad.

Figure 2:
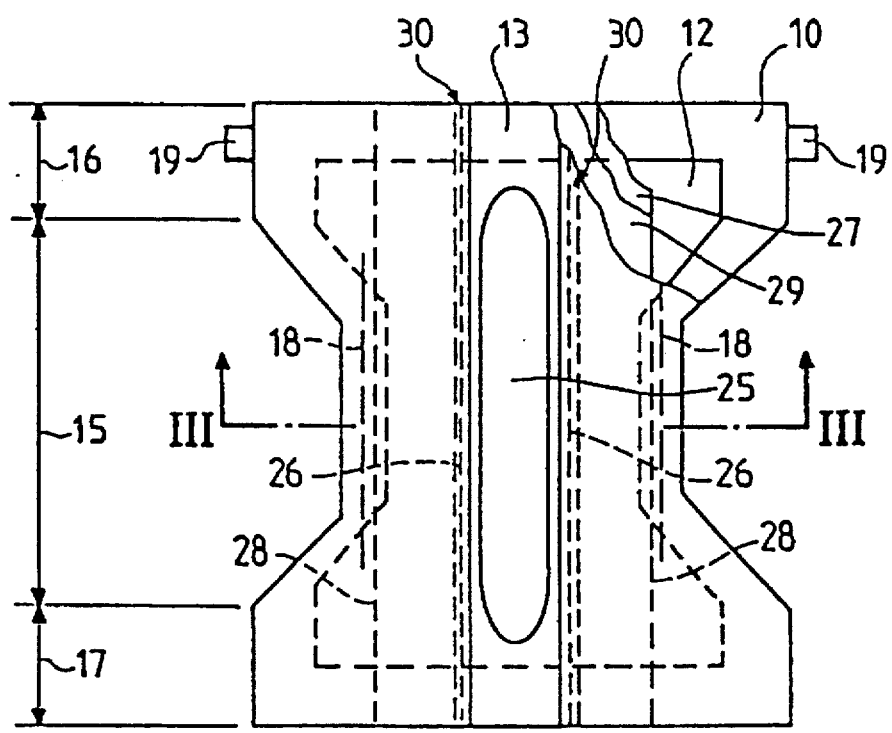
Figure 3:
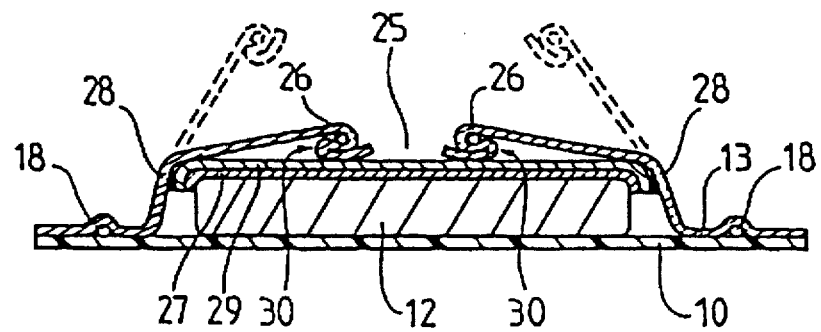

The remainder of the description refers to the attached figures which show, respectively:

FIG. 1, a diagrammatic sectional view of a composite nonwoven material according to the invention;

FIG. 2, a top view, with partial cut away, of an absorbent article of hygiene such as a diaper comprising a crotch region strip consisting of the composite nonwoven material according to the invention and an intermediate strip covering the crotch region strip;

FIG. 3, a view in section along the line III—III of FIG. 2, and

Figure 4:
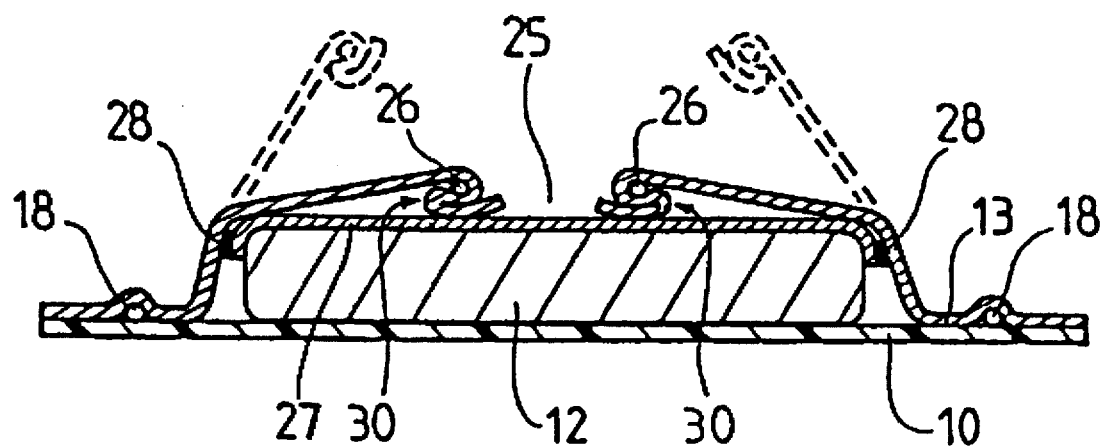

FIG. 4, a sectional view of a diaper similar to that of FIG. 3, but in which the intermediate strip has been left out.

With reference to FIG. 1, a composite nonwoven material 1 according to the invention has been shown diagrammatically in section. This material comprises a first layer 2 consisting of a carded voile of hydrophobic thermoplastic fibers, these fibers being disoriented in at least a proportion of the thickness of the voile so that at least a proportion of the fibers have an angular orientation in relation to the main plane of the fibers of the carded voile and a second layer 3 consisting of a voile made of nonwoven of noncarded type, of hydrophobic thermoplastic fibers.

In the present invention the expression "carded voile" denotes a voile made of nonwoven obtained by the conventional carding technique.

The voiles obtained by carding have the characteristic of the fibers all being substantially oriented in the same main plane, generally the plane of the forward travel of the machine.

According to the present invention the fibers of the carded voile are partially disoriented in relation to the main plane of the fibers of the voile in order that at least in a proportion of the thickness of the voile a certain quantity of fibers should be oriented angularly in relation to this main plane of fibers. The disoriented fibers preferably form an angle of at least 35° in relation to the main plane of the fibers. The disoriented fibers of the carded voile preferably form an angle of between 45° and 90° in relation to the main plane of the fibers.

Such a disorientation of the fibers can be obtained directly during the manufacture of the carded voile by the use of a pseudocard. These pseudocards are pieces of equipment which are known per se and are sold commercially, for example, by the Fehrer company.

The proportion of disoriented fibers of the carded voile is generally at least 20% by weight, preferably from 25% to 85% by weight relative to the total weight of the fibers of the voile.

This disorientation of a proportion of the fibers of the carded voile increases the speed of crossing of the composite material by liquids.

Any thermoplastic and hydrophobic textile fibers may be employed for the carded voiles for those made of nonwoven of noncarded type, such as fibers of high melting point, fibers with a low melting point, two-component fibers, fibers mixed with a binder, such as a heat-reactivable adhesive or a polymer powder of low melting point, and mixtures of fibers of high melting point with fibers with a low melting point, and of two-component fibers.

In the present invention the hydrophobic thermoplastic fibers may be conventionally coated with a spinning finish which contains lubricants, and antistatic and wetting agents. The wetting agents promote the initial passage of the liquids through the composite material.

In the present invention "fibers of high melting point" denote fibers whose composition is such that they do not bond under the effect of moderate heating (heat-melting), for example by reactivation with hot air. Such fibers are, for example, polyester or polyamide fibers.

"Fibers with a low melting point" denote fibers whose composition is such that they soften or melt superficially under the effect of moderate heating and thus bind together (heat-melting). Such fibers are, for example, polyolefin fibers such as polyethylene, polypropylene and ethylene-propylene copolymer fibers.

The two-component fibers are fibers comprising a core made of a polymer of relatively high melting point surrounded by another polymer with a relatively low melting point permitting a melting or a softening of the surface of the fiber under the effect of moderate heating, such as hot-air heating. Such fibers are well known in the art. An example of two-component fibers is a fiber containing a polyester core encased in polyolefin, for example polyethylene.

A "binder" denotes any product which, when mixed with the fibers gives them the possibility of bonding together during moderate heating (heat-melting) for example by calendering or blowing hot air. Heat-reactivable adhesives and powders with a low melting point may be mentioned among these binders.

Heat-reactivable adhesives are well known in the art, and an example of such an adhesive is an aqueous solution of the EVA, EBA or acrylic type.

Similarly, powders of low melting point which can be employed in the present invention are well known in the art and are generally powders of polymers with a low melting point, such as, for example, a polyethylene powder.

The carded voiles and those made of nonwoven of noncarded type of the composite material of the invention may each consist of fibers of the same kind or of different kinds and of identical or different counts.

The carded voile preferably has a weight per unit area of between 20 and 60 g/m², in particular 50 g/m², and the voile of noncarded type preferably has a weight per unit area lower than 20 g/m², for example 15/gm².

According to the invention at least one of the layers of the composite consists of two-component, hydrophobic thermoplastic fibers with a low melting point, mixed with a binder or of a mixture of these fibers with hydrophobic thermoplastic fibers of high melting point. The voile made of nonwoven of noncarded type preferably consists of fibers with a low melting point, such as polypropylene fibers, and the carded voile consists of a mixture of fibers of high melting point and of fibers with a low melting point or of two-component fibers, or else one of the voiles is coated on one of its faces with a heat-reactivable adhesive.

Preferably, furthermore, each of the voiles consists of a mixture of fibers of high melting point, such as polyester fibers, with fibers with a low melting point, such as polyolefin, for example polyethylene, fibers, or two-component fibers or else fibers mixed with a binder such as a heat-reactivable adhesive or a powder of low melting point. The proportion of fibers with a low melting point or of two-component fibers, in the case of a voile consisting of a mixture of fibers, or else the quantity of binder mixed with the fibers or deposited on one of the faces of the voile(s) is generally between 5 and 30% by weight relative to the total weight of the voile.

The layers made up of carded voile 2 and of nonwoven voile of noncarded type 3 are bonded by heat-melting, that is to say by moderate heating of the layers by any means known in the art, such as blowing hot air, calendering, ultrasonic bonding and by infrared radiation. The temperature and the duration of application of heat must be sufficient to ensure bonding of the fibers by softening or superficial melting of the fibers with a low melting point, of the component with a low melting point of the two-component fibers or of the binder, but insufficient to cause a degradation of the fibers of the layers. The bonding temperature is preferably between 120° and 150° C.

Bonding by blowing air and by calendering are particularly recommended, for example by running the layers of the composite through an adhesive-backing calender of the Storck type which has a roll at a temperature of 120°–150° C. This second process is particularly suitable when one of the voiles of the composite comprises a face coated with a binder. In this case quite obviously the voile in which one face is coated with binder is bonded by this face to the other voile of the composite.

The carded voile forming the first layer of the composite may itself comprise a number of layers of carded voile, which are bonded together by heat-melting, and consequently an appropriate number of layers of the composite carded voile will comprise fibers with a low melting point, two-component fibers, fibers mixed with a binder or will have one face coated with a binder to permit the heat-melting bonding of the layers of the carded voile.

The layers of the carded composite voile may consist of fibers of identical or different nature and may have identical or different counts.

The process of manufacture according to the invention of a composite nonwoven material comprises:

the formation of a carded voile made of hydrophobic thermoplastic fibers;

the disorientation of the fibers of the carded voile to obtain in at least a proportion of the thickness of the voile an angular orientation of a proportion of the fibers in relation to the main orientation of the fibers of the carded voile;

the application or deposition of the carded voile onto a voile made of nonwoven of noncarded type made of hydrophobic thermoplastic fibers; and bonding of the voiles by heat-melting to form a composite nonwoven material comprising a first layer of a carded voile with partially disoriented fibers and a second layer of a voile made of nonwoven of noncarded type, the first and second layers being bonded solely by heat-melting.

In a recommended process the carded voile with partially disoriented fibers is obtained by means of a pseudocard, for example of K12 or K21 type from the Fehrer company. The use of a pseudocard for the manufacture of the carded voile makes it possible to form the carded voile and to disorient a proportion of the fibers in a proportion of the thickness of the voile in a single stage.

It is also possible to perform the operation in two separate stages, by first forming the carded voile by means of a card and then by disorienting a proportion of the fibers by any appropriate mechanical means.

Examples of embodiment of composite nonwoven materials according to the invention

EXAMPLE 1

A carded voile is formed by means of a pseudocard, containing partially disoriented fibers comprising a mixture of 6-decitex (deniers) polyester fibers with 3.3-decitex (deniers) polyethylene fibers and with a weight per unit area of 50 g/m² and is superposed onto a voile made of nonwoven of the spun-bonded type made of polypropylene fibers, with a weight per unit area of 15 g/m². The proportion of polyethylene fibers in the carded voile is from 5 to 30% by weight relative to the total weight of the carded voile.

The combination of the two voiles is subjected to moderate heating, bypassing through hot air at 120°–150° C., to form a composite nonwoven material comprising a first layer of a carded voile and a second layer of a voile made of nonwoven of the spun-bonded type, the first and second layers being bonded solely by heat-melting.

This material exhibits an excellent liquid passage time, good resistance to rewetting, and does not become fluffy.

Furthermore, when it is employed as surface voile or to complement a surface voile, as crotch region strip, by placing the second layer made of voile of spun-bonded type inwards, that is to say in contact with the user's skin or with the outer surface of the surface sheet, and the layer of carded voile directly over the absorbent pad, an absorbent article according to the invention is obtained which has a suitable softness due to the fineness of the fibers employed for the inner layer, an excellent speed of crossing by liquids, and which does not become fluffy.

EXAMPLE 2

Example 1 is repeated, the polyethylene fibers of the carded voile being replaced with two-component fibers of the same count comprising a polyester core and a polyethylene jacket.

A composite nonwoven material according to the invention is obtained. This material exhibits an excellent liquid crossing time, good resistance to rewetting and does not become fluffy when employed as a surface voile or crotch region strip in an article of hygiene such as a diaper.

EXAMPLE 3

Example 1 is repeated, only 6-decitex polyester fibers being employed for the carded voile. One face of this carded voile is coated with an aqueous emulsion of ethylene butyl acetate (EBA) at a rate of 4 g of emulsion per square meter of voile. The carded voile is then bonded via its coated face to the polyethylene voile in an adhesive-backing calender of Storck type in which the heating roll is at a temperature of 120°–150° C.

A composite nonwoven material according to the invention is obtained.
Example of Embodiment of an Absorbent Article of Hygiene According to the Invention.

FIGS. 2 and 3 show, by way of example, an absorbent article of hygiene such as a diaper, comprising a crotch strip consisting of a composite nonwoven material according to the invention.

The diaper shown in FIGS. 2 and 3 comprises, in a manner known per se, a support sheet 10 which is impervious to liquids, an absorbent pad 12, for example made of cellulose fluff pulp, optionally with incorporation of so-called superabsorbent polymeric materials, a crotch region strip 27, an intermediate strip 29 similar in size to that of the crotch region strip 27, arranged directly on this crotch region strip and generally consisting of a conventional nonwoven (for example of spun-bonded type) and a surface sheet 13, for example a voile of hydrophobic nonwoven. The two sheets 10 and 13 are of the same size and have the same hourglass shape, that is to say a rectangular shape with two opposite side cutouts defining, in the lengthwise direction of the diaper, a crotch region 15 of reduced width between two end regions 16 and 17 of increased width. The absorbent pad 12 arranged between the two sheets 10 and 13 is also hourglass-shaped but of smaller size than the sheets 10 and 13 which are joined to each other, for example by adhesive bonding along the whole periphery of the pad 12.

First lengthwise elastic members 18, each consisting, for example, of one or several elastic strands or yarns or of an elastic strip, are attached in the stretched state to the support sheet 10, at least in the crotch region 15 between the back of the cutouts in the sheet 10 and the back of the corresponding cutouts in the absorbent pad 12.

Furthermore, adhesive fastenings 19 are attached to the opposite side edges in the end region 16 forming the rear part of the diaper.

The surface sheet 13 comprises, in its middle part, a middle lengthwise cutout 25 to form an opening, preferably of oblong shape. The width of the opening is markedly smaller than the width of the pad 12, preferably smaller than one half of the width of the pad 12 in the crotch region. Furthermore, the surface sheet 13 comprises, over its whole length, two Z-shaped double folds 30 in a downward direction (toward the pad 12) which are arranged on each side of the opening 25, and elastic members 26 are attached in the stretched state by adhesive bonding in the upper back-folds of these double folds 30, the two back-folds of each double fold 30 being integrally joined to one another by adhesive bonding or any other means so as to consolidate or stiffen the cover sheet 13 at this point and thus to facilitate cutting out and removing the material from the opening 25, which is performed subsequently. The crotch region strip 27 of composite nonwoven material according to the invention is arranged directly above the absorbent pad along the whole length of the diaper and is at least as wide as the absorbent pad 12 in the crotch region. The crotch region strip 27 is bonded to the absorbent pad 12 and/or to the intermediate strip 29 by any suitable well-known means, and the intermediate strip 29, in the embodiment shown, is attached to the surface sheet 13, on the one hand on the two transverse edges of the diaper and, on the other hand, along two lengthwise lines 28, for example lines of adhesive bonding, which are situated in a position that is slightly offset in relation to the lengthwise edges of the absorbent pad 12 in the crotch region 15.

Although the surface sheet has been shown as comprising two Z-shaped double folds 30, it is also possible to modify the shape of these folds in any appropriate manner, for example by producing folds which are S-shaped.

Equally, the elastic members 26 can be arranged in any suitable place other than the upper back-folds, for example the lower back-folds.

The crotch strip 27 consists of a composite nonwoven material according to the invention, comprising a first layer of a carded voile with partially disoriented fibers and a second layer of a voile made of nonwoven of noncarded type, the first and second layers being bonded only by heat-melting, the first layer being in direct contact with the absorbent pad 12.

FIG. 4 is a sectional view similar to that of FIG. 3, of a recommended embodiment of a diaper according to the invention. This embodiment is identical with that of FIGS. 2 and 3, except that the intermediate voile 29 has been eliminated. The crotch region strip 27 in this embodiment is arranged on the absorbent pad 12 with the carded layer in contact with the pad. The upper layer made of voile of nonwoven of noncarded type of the crotch region strip is bonded to the cover sheet along two lengthwise lines 28, for example lines of adhesive bonding, similar to those of FIG. 3. In this embodiment the layer made of nonwoven of noncarded type, which is situated directly below the cutout 25, will be directly in contact with the user's skin.

This diaper exhibits a high rate of crossing by liquids, good resistance to rewetting and does not become fluffy.

I claim:

1. Composite nonwoven material characterized in that it comprises at least one layer (2) made of a carded voile of hydrophobic thermoplastic fibers, the said fibers being partially disoriented in at least a proportion of the thickness of the voile so that a proportion of the said fibers has an angular orientation in relation to the main plane of the fibers of the said voile, and a layer (3) made of a voile of nonwoven of noncarded type, of hydrophobic, thermoplastic fibers, the fibers of at least one of the layers being chosen from fibers with a low melting point, two-component fibers, mixtures of such fibers with fibers of high melting point and fibers mixed with a binder, or at least one of the layers is made of a voile one face of which is coated with a binder, the two layers being bonded to each other solely by heat-melting.

2. Material according to claim 1, characterized in that the proportion of disoriented fibers in the layer (2) of carded voile is at least 20% by weight relative to the total weight of the fibers of the voile.

3. Material according to claim 1, characterized in that the layer of carded voile has a weight per unit area of between 20 and 60 g/m² and the layer of voile of nonwoven of noncarded type has a weight per unit area lower than 20 g/m².

4. Material according to claim 1, characterized in that the fibers of at least one of the layers consist of a mixture of polyester fibers with fibers chosen from fibers with a low melting point and two-component fibers.

5. Material according to claim 4, characterized in that the fibers with a low melting point are chosen from polyethylene, polypropylene and ethylene/propylene copolymer fibers.

6. Material according to claim 1, characterized in that the fibers mixed with a binder are polyester fibers mixed with a heat-reactivable adhesive or a powder with a low melting point.

7. Material according to any one of claims 1 to 5, characterized in that the two-component fibers or the fibers with a low melting point constitute 5 to 30% by weight relative to the total weight of the voile.

8. Material according to claim 1, characterized in that the quantity of binder mixed with the fibers or deposited on one face of one of the said voiles is between 5 and 30% by weight relative to the total weight of the voile.

9. Material according to claim 1, characterized in that the carded voile is a composite voile comprising at least two layers of carded voile bonded together by heat-melting.

10. Process for the manufacture of a composite nonwoven material, characterized in that it comprises the stages consisting in:

forming a carded voile of hydrophobic thermoplastic fibers;

partially disorienting the fibers of the carded voile to obtain in at least a proportion of the thickness of the carded voile an angular orientation of the fibers in relation to the main plane of the fibers of the carded voile;

forming a voile made of nonwoven of noncarded type, of hydrophobic thermoplastic fibers;

superposing the carded voile with partially disoriented fibers and the voile made of nonwoven or noncarded type to obtain a first layer of carded voile and a second layer of voile made of nonwoven of noncarded type, the fibers of at least one of the layers being chosen from fibers with a low melting point, two-component fibers, mixtures of such fibers with fibers of high melting point and fibers mixed with a binder; and bonding the layers together by heat-melting.

11. Process according to claim 10, characterized in that the bonding by heat-melting comprises a reactivation by hot air passing through the layers.

12. Process for the manufacture of a composite nonwoven material, characterized in that it comprises the stages consisting in:

forming a carded voile of hydrophobic thermoplastic fibers;

partially disorienting the fibers of the carded voile to obtain in at least a proportion of the thickness of the carded voile an angular orientation of the fibers in relation to the main plane of the fibers of the carded voile;

forming a voile made of nonwoven of noncarded type, of hydrophobic thermoplastic fibers, coating one of the faces of one of the said voiles with a binder;

superposing the carded voile with partially disoriented fibers and the voile made of nonwoven of noncarded type to obtain a first layer of the carded voile and a second layer of the voile made of nonwoven of non-carded type so that the said binder-coated face forms an interface between the said layers; and bonding the layers to each other by heat-melting.

13. Process according to claim 12, characterized in that the bonding of the said layers by heat-melting is carried out by calendering the layers by means of an adhesive-backing calender.

14. Process according to claim 10, characterized in that the stage of partial disorientation of the fibers of the carded voile comprises the angular disorientation, in relation to the main plane of the fibers, of at least 20% by weight of fibers in relation to the total weight of the fibers of the voile.

15. Process according to either of claims 13 to 14, characterized in that the angle of disorientation of the fibers in relation to the main plane of the fibers is at least 35°.

16. Process according to claim 10, characterized in that the stage of formation of the carded voile and the stage of partial disorientation of the fibers of the said voile are carried out jointly by means of a pseudocard.

17. Absorbent article of hygiene comprising an outer layer which is impervious to body fluids (10), an absorbent pad (12) which is permeable to body fluids and attached to the outer layer, the outer layer (10) and the absorbent pad (12) comprising widened end parts (16, 17) joined by a crotch region (15) of smaller width, a preferably hydrophobic surface sheet (33), and a crotch region strip which is permeable to body fluids (27) and arranged between the absorbent pad (12) and the surface sheet (13) and of width similar to the width of the pad in the crotch region and of length which is at least equal to the length of the pad and bonded to the pad, characterized in that the crotch region strip consists of the composite material according to any one of claims 1 to 9, the layer made of carded voile being directly in contact with the absorbent pad.

18. Absorbent article of hygiene according to claim 17, in which the surface sheet (13) comprises a medium lengthwise cutout (25) forming an opening, preferably of oblong shape.

19. Absorbent article of hygiene according to claim 17, additionally comprising an intermediate strip (29) of nonwoven, similar in size to the crotch region strip and arranged directly on the crotch region strip.

* * * * *